United States Patent [19]
Naito et al.

[11] Patent Number: 4,460,765
[45] Date of Patent: Jul. 17, 1984

[54] ENZYME INHIBITOR PRODUCED BY CULTIVATION OF STREPTOMYCES MICROORGANISMS

[75] Inventors: Atsushi Naito; Fumio Nakagawa; Takao Okazaki; Akira Terahara; Seigo Iwado; Mitsuo Yamazaki, all of Tokyo, Japan

[73] Assignee: Sankyo Company Limited, Tokyo, Japan

[21] Appl. No.: 377,435

[22] Filed: May 12, 1982

Related U.S. Application Data

[63] Continuation-in-part of Ser. No. 204,473, Nov. 6, 1980, abandoned.

[30] Foreign Application Priority Data

Nov. 10, 1979 [JP] Japan .................... 54-145701

[51] Int. Cl.$^3$ ............ C12D 19/40; C07H 17/02; C12P 17/18; C12R 1/465
[52] U.S. Cl. ........................ 536/26; 435/88; 435/119; 435/128; 435/253; 435/886; 536/24; 544/277
[58] Field of Search .............. 435/87, 88, 89, 92, 435/128, 119, 121, 122, 126, 169, 253, 886; 424/116, 118; 544/277; 536/24, 26

[56] References Cited

U.S. PATENT DOCUMENTS 4,104,462  8/1978  Fisher et al. ................ 536/24

FOREIGN PATENT DOCUMENTS 29329     5/1981   European Pat. Off. ....... 435/169
52-18893  2/1977   Japan ............................ 435/121
912790    12/1962  United Kingdom .......... 435/886

OTHER PUBLICATIONS

Amer et al, "Cyclic Nucleotide Phosphodiesterases: Properties, Activators Inhibitors, Structure–Activity RElationships and . . . ", Journal of Pharmaceutical Sciences 64(1) (1975) pp. 1–37.
Shuman et al, "Synthesis and Biological Activity of Some Purine 5'-thio-5'-deoxynucleoside 3', 5'-cyclic Phosphothionates", Biochemistry 12(15) (1973) pp. 2781–2786.

Primary Examiner—Thomas G. Wiseman
Assistant Examiner—John E. Tarcza
Attorney, Agent, or Firm—Frishauf, Holtz, Goodman & Woodward

[57] ABSTRACT

A new compound, named "Griseolic acid", and its salts and can be prepared by the cultivation of *Streptomyces griseoaurantiacus* SANK 63479 (FERM-P 5223). Griseolic acid and its salts inhibit the activity of the enzyme cyclic adenosine monophosphate phosphodiesterase and, as a result of this, have variety of physiological activities and uses.

7 Claims, 3 Drawing Figures

ENZYME INHIBITOR PRODUCED BY CULTIVATION OF STREPTOMYCES MICROORGANISMS

CROSS-REFERENCE TO RELATED APPLICATIONS

This application is a continuation-in-part application of U.S. Ser. No. 204,473 filed on Nov. 6, 1980 now abandoned.

BACKGROUND OF THE INVENTION

The present invention relates to a new compound, named griseolic acid, and salts thereof having activity as an enzyme inhibitor, and to a process for preparing them.

Specifically, griseolic acid and its salts inhibit the activity of cyclic adenosine monophosphate (cAMP) phosphodiesterase (PDE) and can thus increase the level of cAMP in the cells of the patient being treated.

It is well-known that cAMP, which is very widely distributed in animal tissues, functions as a second messenger for and mediates the effect of a large number of hormones; as a result, cAMP has a variety of very important physiological and biochemical roles. Additionally, it is known to have an effect on: division, growth and differentiation of cells; systole; haemapoiesis; various activities of the central nervous system; immune reactions; and liberation of insulin and histamine. Its concentration in tissues and hence its effect on these various functions depends upon the balance between the enzyme which synthetizes cAMP (adenylic acid cyclase) and the enzyme which splits cAMP (cAMP PDE). As inhibitor against cAMP PDE, griseolic acid and its salts would increase the level of cAMP in the cells and provide physiological activity of the type that is of value as an angiocardiokinetic agent, for example, as disclosed in U.S. Pat. No. 4,104,462 for the adenosine nitrates disclosed therein, an antiasthmatic agent, a smooth muscle relaxant, an antiinflammatory agent, a treatment of diabetes and a treatment of various types of psoriasis.

BRIEF SUMMARY OF THE INVENTION

It is, therefore, an object of the invention to provide, as a new composition of matter, a compound having an inhibitory effect against cAMP PDE.

It is a further object of the invention to provide a process for producing such an inhibitory compound by the cultivation of an appropriate microorganism of the genus Streptomyces.

The new compound of the invention is named griseolic acid and can be characterized by the following chemical structure and physico-chemical properties:

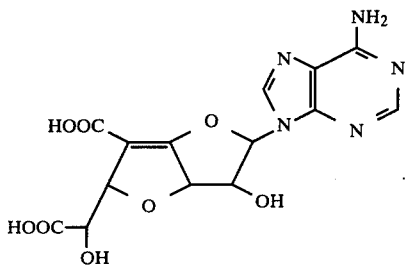

1. Colour and state:
   White powder.
2. Melting point:
   Over 220° C. (decomposition).
3. Molecular weight:
   379 (by high resolution mass spectrometry).
4. Molecular formula:
   $C_{14}H_{13}N_5O_8$.
5. Colour reactions:
   Positive for iodine, 2,4-dinitrophenylhydrazine and Bial's reagent. Negative for ferric chloride and ninhydrin.
6. Optical rotation:
   $[\alpha]_D^{20} = +6.9°$ [as its free acid, C=1.0, dimethyl sulphoxide];
7. Ultraviolet absorption spectrum:
   The ultraviolet absorption spectra, as measured in 0.1N hydrochloric acid and 0.1N aqueous sodium hydroxide, are shown in FIG. 1 of the accompanying drawings.
8. Infrared absorption spectrum:
   The infrared absorption spectrum measured in a KBr pellet is as shown in FIG. 2 of the accompanying drawings.
9. Nuclear magnetic resonance spectrum:
   Nuclear magnetic resonance spectrum as measured in hexadeuterated dimethyl sulphoxide at 60 MHz is shown is FIG. 3 of the accompanying drawings.

The salts of griseolic acid may include, typically, alkali metal salts, for example, sodium, potassium and lithium salts; ammonium salt; alkaline earth metal salts, for example, calcium, magnesium and barium salts; and the like. The sodium and calcium salts are preferable. It is to be noted that the salts of griseolic acid are also new compounds and forming part of the present invention.

DETAILED DESCRIPTION OF INVENTION

Figure 1:
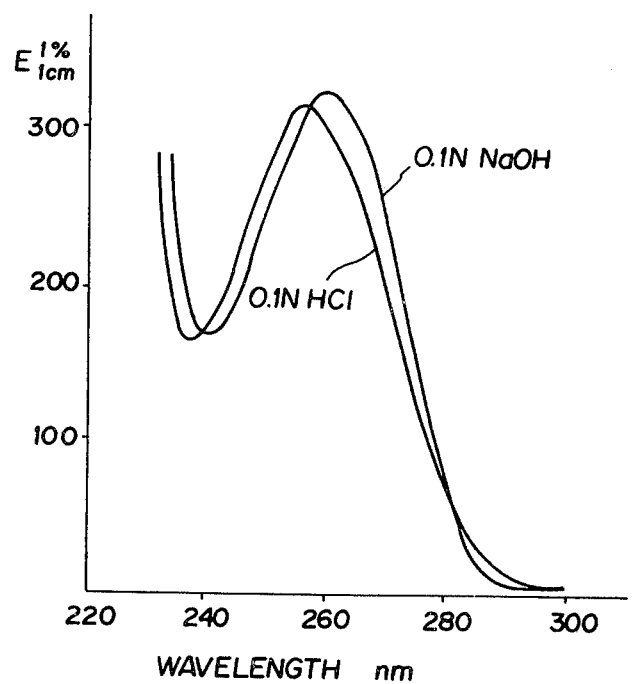
Figure 2:
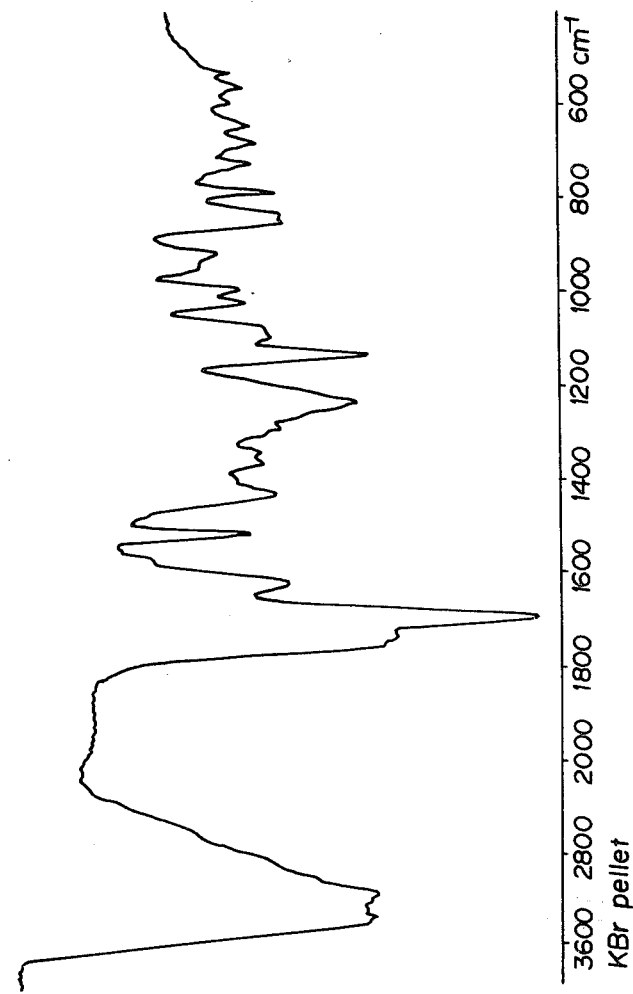
Figure 3:
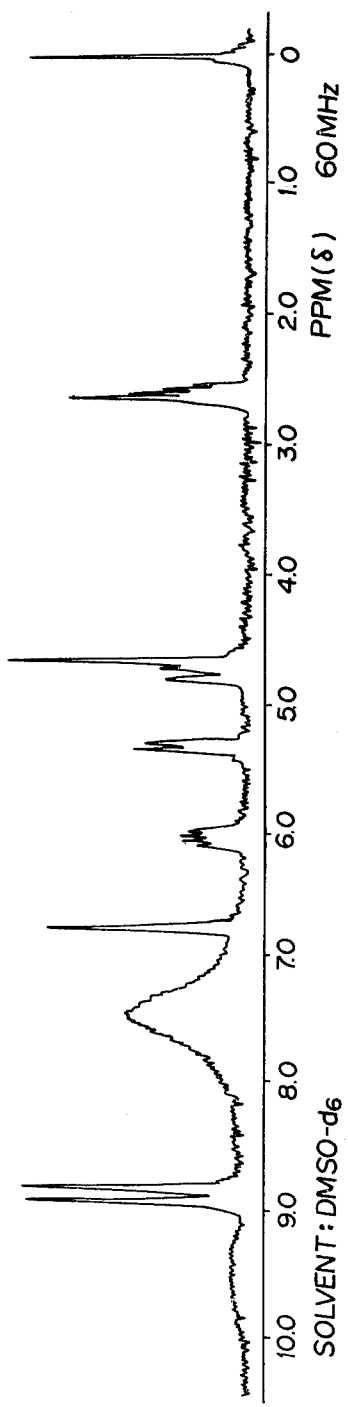

We have found that griseolic acid and its salts can be prepared by cultivating a griseolic acid-producing microorganism of the genus Streptomyces and separating the griseolic acid or a salt thereof from the fermented broth.

In particular, we have found that these compounds can be prepared by culturing a strain of actinomycetes hereinafter referred as "Strain No. SANK 63479", which has been newly isolated from soil samples taken from Kyoto in Japan.

IDENTIFICATION OF STRAIN NO. SANK 63479

Strain No. SANK 63479 was identified according to ISP (International Streptomyces Project) standards, the examination standards for the applied microbiological industry, Bergey's Manual (8th edition), "The Actinomycetes" by S. A. Waksman, and "Actinomycetes" by Krasilinikov, as well as other recent literature concerning the taxonomy of the actinomycetes.

Strain No. SANK 63479 is found to form spiral sporephores having a chain of 10 to 50 or even more spores. The spores have smooth surfaces and aerial mycelium grows on various madia. The aerial hyphae are simply branched.

Strain No. Sank 63479 was deposited and assigned the strain designation NRRL 12314 on Oct. 22, 1980.

The strain thus possesses properties similar to those of *Streptomyces griseoaurantiacus*. For the purpose of comparative tests, we used the type strain ATCC 19840 of *Streptomyces griseoaurantiacus* (Krassilnikov and Yuan 1965) Pridham 1970.

1. Morphological characteristics
As shown in Table 1.

TABLE 1

|  | Strain No. SANK 63479 | ATCC 19840 |
| --- | --- | --- |
| Form of sporephores | spiral | spiral |
| Surface of spores | smooth | smooth |
| Branching of aerial hyphae | simply branched | simply branched |
| Number of spores | 10 to 50 or more | 10 to 50 or more |
| Special organs | none | none |

2. Growth on various media

The two strains were cultivated at 28° C. for 14 days on various agar plate media and exhibited the properties shown in Table 2.

TABLE 2

| Agar medium | Strain No. SANK 63479 | ATCC 19840 |
| --- | --- | --- |
| Yeast malt agar (ISP-2): | | |
| Growth | Very good, dull reddish orange | Good, pale yellowish orange |
| Aerial mycelium | Abundant, grey | Abundant, grey |
| Reverse surface | Dull reddish orange | Yellowish orange |
| Soluble pigment | None | None |
| Oatmeal agar (ISP-3): | | |
| Growth | Very good, dull orange | Very good, light reddish orange |
| Aerial mycelium | Abundant, grey | Good, grey |
| Reverse surface | Dull red | light reddish orange |
| Soluble pigment | None | None |
| Starch-inorganic salt agar: (ISP-4) | | |
| Growth | Very good, dull orange | Very good, brown to pink |
| Aerial mycelium | Abundant, brownish white | Abundant, light brownish white |
| Reverse surface | light brown | Pink to dark reddish brown |
| Soluble pigment | None | None |
| Glycerine-asparagate agar: (ISP-5) | | |
| Growth | Very good, dull red | Good, pale brown to pink |
| Aerial mycelium | Abundant, light brownish white | Abundant, light brownish white |
| Reverse surface | Dull red | Pale brown to pink |
| Soluble pigment | None | None |
| Tyrosine agar: (ISP-7) | | |
| Growth | Very good, dull red | Good, yellowish brown |
| Aerial mycelium | Abundant, brownish white | Abundant, light brownish white |
| Reverse surface | Brownish purple | Dark brown |
| Soluble pigment | None | None |
| Sucrose-nitrate agar: | | |
| Growth | Good, dull reddish orange | Moderate, light reddish orange |
| Aerial mycelium | Abundant, light brownish white | Good, light brownish white |
| Reverse surface | Dull reddish orange | Pale reddish orange to pale reddish brown |
| Soluble pigment | Pale purple (slight) | Pale purple (slight) |
| Glucose-asparagate agar: | | |
| Growth | Good, dull red | Moderate, pale yellowish brown |
| Aerial mycelium | Abundant, grey | Good, light brownish white |
| Reverse surface | Dull red | Brownish white |
| Soluble pigment | Pale purple (slight) | None |
| Nutrient agar (Difco): | | |
| Growth | Good, pale yellowish brown | Good, pale brown |
| Aerial mycelium | Scarce, brownish white | Good, light brownish white |
| Soluble pigment | None | None |

3. Physiological properties

The physiological properties of the two strains are shown in Table 3. Three media were used to determine the production of melanoid pigments: tryptone-yeast extract broth (ISP-1), peptone extract-iron agar (ISP-6) and tyrosine agar (ISP-7). The results are reported as either positive (+) or negative (−).

TABLE 3

|  | Strain No. SANK 63479 | ATCC 19840 |
| --- | --- | --- |
| Reduction of nitrate | + | + |
| Hydrolysis of starch | + | − |
| Liquefaction of gelatin | + | + |
| Coagulation of milk | + | + |
| Peptonization of milk | − | − |
| Production of melanoid pigments | − | − |

4. Utilization of carbon sources

The utilization of carbon sources is as shown in Table 4. The culture medium employed was Pridham-Gottlieb agar (ISP-9) and evaluations were conducted after cultivation at 28° C. for 14 days. The results are reported according to the following code:

++: well utilized;
+: utilized;
±: poorly utilized
−: not utilized.

TABLE 4

|  | Strain No. SANK 63479 | ATCC 19840 |
| --- | --- | --- |
| D-glucose | ++ | ++ |
| L-arabinose | + | ++ |
| D-xylose | ± | ± |
| D-fructose | ++ | + |
| L-rhamnose | ++ | ++ |
| i-inositol | ± | − |
| galactose | ++ | ++ |
| mannose | ++ | + |
| sucrose | − | − |
| D-cellobiose | ++ | ± |
| lactose | ++ | ± |
| maltose | ++ | ± |
| raffinose | − | − |
| D-mannitol | ++ | ++ |
| insulin | − | − |
| dextrin | ++ | ++ |
| soluble starch | ++ | ± |
| salicin | − | − |
| sodium succinate | + | ± |
| glycerine | ++ | + |
| cellulose | + | ± |

TABLE 4-continued

| | Strain No. | |
|---|---|---|
| | SANK 63479 | ATCC 19840 |
| control | — | — |

It can be seen from the results reported above that there are considerable points of similarity in morphological properties, physiological properties and carbon source utilization between Strain No. SANK 63479 and the type strain *Streptomyces griseoaurantiacus* ATCC 19840. Accordingly, Strain No. SANK 63479 has been identified as *Streptomyces griseoaurantiacus* (Krasilinikov and Yuan 1965) Pridham 1970. This strain was deposited on Oct. 9, 1979, at the Fermentation Research Institute, Agency of Industrial Science and Technology, Japan, from which it is available under the Accession No. FERM-P 5223, and on Oct. 22, 1980 at the Agricultural Research Service, Peoria, U.S.A., from which it is available under the Accession No. NRRL 12314.

The inhibitory activity of the compounds of the invention (or of compositions, e.g. culture broths, containing them) may be assayed by the method of Pichard and Thun [Journal of Biological Chemistry, 251, 5726–5737 (1976)], using a crude enzyme solution derived from rat brains as the cAMP PDE. In this method, $^{14}C$-labelled cAMP is used as the substrate and is reacted at 30° C. for 20 minutes with 2–5 $\mu l$ of the compound or composition under test, 20 $\mu l$ of a snake venom and 40 $\mu l$ of the crude enzyme solution in a 0.2M tris-HCl buffer (pH 8.0). The tris-HCl buffer is a mixture of tris(hydroxymethyl)aminomethane and hydrochloric acid. After completion of the reaction, the reaction mixture is treated with an Amberlite (Trade Mark) IRP-58 resin. From the residual radioactivity of the adenosine in the product, the inhibitory activity of the compound or composition against the cAMP PDE can be calculated as a percentage.

As is well-known, the properties of actinomycetes, including Streptomyces, strains are not fixed and they readily undergo mutation both through natural causes and as the result of artificial mutation. Although the invention relates to the production of griseolic acid and its salts especially by the cultivation of the above identified *Streptomyces griseoaurantiacus* SANK 63479, it also includes within its scope the use of mutants of this organism and generally of any Streptomyces strain which is capable of producing griseolic acid and its salts.

The cultivation of the griseolic acid-producing microorganism, in accordance with the process of the invention, can be performed under the conditions conventionally employed for the cultivation of Actinomycetes strains. Shaken culture in a liquid medium or a solid cultivation method are preferred.

The nutrient medium used for the cultivation can be of a composition such as is conventionally used for the cultivation of Actinomycetes. Thus, it would contain an assimilable carbon source and an assimilable nitrogen source. Suitable assimilable carbon sources include: a concentrated solution of a sugar (e.g. of sucrose and/or invert sugar or of a mixture of sucrose with another sugar, such as glucose or corn syrup), starch, dextrose, mannitol, fructose, galactose or rhamnose or any combination of two or more thereof. The nitrogen source may be: an organic or inorganic compound, e.g. ammonium chloride, ammonium sulphate, urea, ammonium nitrate or sodium nitrate; or natural products, such as peptone, meat extract, yeast extract, dried yeast, live yeast, corn steep liquor, soybean powder, soybean flour, casamino acid or soluble vegetable proteins. A single such nitrogen source or a combination of any two or more may be employed. In addition, the nutrient medium may also contain inorganic salts(such as potassium chloride, calcium carbonate or phosphoric acid salts), optionally together with other organic or inorganic substances to promote the growth of the microorganism or its production of griseolic acid and/or salt thereof.

The method of cultivation may be a liquid cultivation method, with reciprocal or rotatory shaking, or a solid cultivation method, a deep-stirring cultivation method being particularly preferred. Although the microorganism will grow over a wide range of temperatures, it is particularly preferred to effect the cultivation at a temperature of from 20° to 35° C. and at a substantially neutral pH value. When a liquid cultivation method is employed, the cultivation is normally effected for a period of from 48 hours to 120 hours, during which time griseolic acid and/or a salt thereof is formed and accumulates in the culture broth. The progress of the cultivation may be monitored and the content of griseolic acid in the broth estimated by determining the enzyme inhibitory activity of the broth using the method described above. After completion of deep liquid cultivation, the culture broth will generally show an inhibitory activity of from 70 to 85%.

Griseolic acid is an acidic, water-soluble substance and normally and preferably exists in the culture broth in the form of its calcium salt. It is, therefore, possible to employ methods of separation and purification of the type commonly used for the isolation of water-soluble microorganism metabolic products. In the case of the deep cultivation method, the preferred separation and purification procedure is as follows. First, the cells of the microorganism are separated by filtration or centrifugation and the resulting filter cake is washed with water. The washings and the filtrate or supernatant liquor from centrifugation are combined and the combined liquor is treated, in turn, with activated charcoal or another adsorbent and an ion-exchange resin. The adsorption may be conducted either batch wise or by continuously feeding the liquor through an adsorption column. In the batch method, for example, an activated charcoal adsorbent is preferably added in an amount of from 0.1 to 0.6% w/v, more preferably from 0.35 to 0.40% w/v, to the filtrate and the resulting mixture is stirred for a period of time of from 30 to 60 minutes.

The activated charcoal adsorbent is then eluted with aqueous acetone or an aqueous lower alkanol and the eluate is concentrated by evaporation under reduced pressure. The residue is then further purified by means of ion-exchange resins, an activated charcoal column and a Sephadex column to give pure griseolic acid having the properties hitherto described.

The inhibitory activity of griseolic acid against cAMP PDE in terms of its 50% inhibitory value ($I_{50}$) are shown in Table 5 against cAMP PDE from a variety of sources having either a high or a low Michaelis constant ($K_m$). The results are reported as $\mu$moles ($\mu M$).

TABLE 5

| | low $K_m$ cAMP POE | high $K_m$ cAMP POE |
|---|---|---|
| cAMP concentration in substrate | 0.14 $\mu M$ | 100 $\mu M$ |

TABLE 5-continued

| | low $K_m$ cAMP POE | high $K_m$ cAMP POE |
|---|---|---|
| cAMP POE source: | | |
| rat brain | 0.16 μM | 0.80 μM |
| rat heart | 0.036 μM | 0.34 μM |
| rat aorta | 0.031 μM | 0.51 μM |
| rat platelets | 0.041 μM | 8.0 μM |
| rat kidney | 0.12 μM | 0.58 μM |

As can be seen from the results reported in Table 5, griseolic acid has a remarkably potent and specific inhibitory effect against both high and low Michaelis constant cAMP PDE. By comparison, Papaverine, which is known in the art to be an inhibitor against this enzyme, has an $I_{50}$ value of 3.5 μM against a low Michaelis constant cAMP PDE (cAMP concentration 0.14 μM) derived from a rat brain. Thus, the inhibitory activity of griseolic acid is about 20 times stronger than that of papaverine. Indeed, it is believed that griseolic acid has the strongest inhibitory activity against this enzyme of those natural products hitherto tested. Moreover, basic tests on cytotoxicity using Hela S-3 strain mouse fibroblast cells showed no inhibition of cell growth even at concentrations of 100 μg/ml, thus indicating a probable lack of toxicity to human and other animals.

Griseolic acid or its salt of this invention can be applied for the treatment of various diseases as explained hereinabove. For instance, griseolic acid may be used as an antiasthmatic agent, a smooth muscle relaxant especially for chronic bronchitis and also as an angiocardiokinetic agent for various types of coronarisms caused by arteriosclerosis or thrombus. The compound of this invention may be administered by any conventional means, for example (e.g. by subcutaneous, intravenous or intramuscular injection or topical application) or orally (e.g. in the form of tablets, capsules, powders or granules). The daily dose for adults will, of course, vary depending upon the age, body weight and condition of the patient, as well as upon the route and times of administration. However, the compounds of this invention are in general administered in an amount of 1 to 100 mg/day via oral route or in an amount of 0.1 to 10 mg/day via parenteral route in several divided doses.

The invention is further illustrated by the following non-limiting Examples.

EXAMPLE 1

30 liters of medium having pH of 7.0 before sterilization and the following composition (percentages are w/v) were prepared:

| | |
|---|---|
| Glucose | 5% |
| Soybean powder | 1% |
| Yeast extract | 0.1% |
| Polypeptone | 0.4% |
| Meat extract | 0.4% |
| Sodium chloride | 0.25% |
| Calcium carbonate | 0.5%. |

15 liters of this medium were charged into each of two 30 liter jar fermenters, which were then sterilized under pressure at 121° C. for 30 minutes. After cooling, 150 ml of a culture broth of strain SANK 63479 (which had previously been incubated in the medium described above by means of a rotatory shaking cultivator at 28° C. for 72 hours) were innoculated into each fermenter. Cultivation was then carried out at 28° C. for 72 hours under aeration at the rate of 10 liters/minute and with agitation at 200 rpm. After completion of the cultivation, 2 μl of the culture filtrate was found to exhibit an inhibitory activity of 76%.

The combined filtrates (pH 6.5) from the two jar fermenters, a total amount of 28 liters, were passed through Diaion HP-20 (a trade mark for an ion exchange resin produced by Mitsubishi Chemical Co., Limited) and were then adsorbed on carbon and washed with water, after it was eluted with a 60:40 by volume mixture of acetone and water. After evaporating off the acetone from the eluate, the aqueous solution was concentrated and then subjected to lyophilization to give 120 mg of a crude powder.

This product was dissolved in a samll abount of distilled water and adsorbed on Dowex 1×4 Cl⁻ form (a trade mark for an ion exchanger produced by Dow Chemical Co.) to convert the calcium salt to free griseolic acid. The desired acid was then eluted using various concentrations of aqueous sodium chloride and column chromatography was thereafter repeated using a Sephadex LH-20 resin produced by Pharmacia Co. The active fractions thus obtained were adjusted to a pH value of 3.0 by the addition of 0.1N hydrochloric acid and column chromatography was again repeated using Sephadex LH-20. Finally, the product was subjected to preparative thin layer chromatography using silica gel 60 $F_{254}$ (available from Merck & Co.) with a plate thickness of 0.25 mm developed with a 4:1:2 by volume mixture of butanol, acetic acid and water; Rf value 0.08. There were obtained 31 mg of the desired griseolic acid.

Alternatively, in the procedure described above, an excess of a saturated aqueous solution of calcium hydroxide can be added to the pH-adjusted active fractions and the resulting mixture cooled to 4°-5° C. to separate a precipitate. This precipitate was recovered by filtration, giving 42 mg of the desired calcium salt of griseolic acid. The appearance, melting point, colour reactions and ultraviolet adsorption spectrum are the same as those reported above for the free acid, but this product was confirmed to be the calcium salt by X-ray fluorescence spectrometry, which showed an energy position exactly corresponding to calcium.

EXAMPLE 2

The procedure described in Example 1 was repeated, except that 600 liter tanks, each containing 300 liters of the medium described in Example 1, were employed. After cultivating the microorganism for 48 hours, 5 μl of the culture broth were found to exhibit an inhibitory activity of 76%. The desired product was separated and purified from 280 liters of the culture broth, following the procedure described in Example 1, to give 531 mg of a product showing a single spot on thin layer chromatography using the same plate and developing solvent as in Example 1. The product was then dissolved in 0.1N hydrochloric acid to complete conversion to the free acid and was then subjected to repeated procedures to convert it to the calcium salt. There were finally obtained 400 mg of a pure product having the same properties as that obtained in Example 1.

We claim:

1. Griseolic acid having the formula

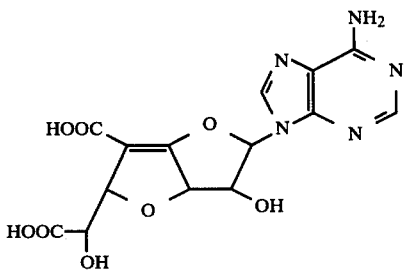

and salts thereof.

2. A process for preparing griseolic acid and salts thereof, which comprises cultivating the microorganism *Streptomyces griseoaurantiacus* SANK 63479, NRRL 12314 in a culture medium therefor and separating griseolic acid or a salt thereof from the resulting culture broth.

3. A process as claimed in claim 2, wherein the cultivation is effected at a temperature of from about 20° C. to about 35° C.

4. A process as claimed in claim 2, in which the cultivation is effected at a pH of about neutrality.

5. A process as claimed in claim 2, wherein the cultivation is effected by a deep stirring cultivation method.

6. A process for the preparation of griseolic acid or a salt thereof, which process comprises cultivating *Streptomyces griseoaurantiacus* SANK 63479, NRRL 12314 in a liquid culture medium therefor by the deep stirring cultivation method at a temperature of from about 20° C. to about 35° C. and at a pH of about neutrality, and separating griseolic acid or a salt thereof from the resulting culture broth.

7. A process as claimed in claim 6, wherein the cultivation is terminated when the culture broth exhibits an inhibitory activity against cAMP PDE derived from rat brains of from 70 to 85%.

* * * * *